United States Patent
Glass et al.

[11] Patent Number: 5,938,595
[45] Date of Patent: Aug. 17, 1999

[54] FIBER OPTIC D DIMER BIOSENSOR

[75] Inventors: Robert S. Glass, Livermore; Sheila A. Grant, Pleasanton, both of Calif.

[73] Assignee: The Regents of the University of California, Oakland, Calif.

[21] Appl. No.: 08/653,183

[22] Filed: May 24, 1996

[51] Int. Cl.[6] .................................................. A61B 5/00
[52] U.S. Cl. ............................ 600/342; 600/341; 356/39
[58] Field of Search ......................... 128/633, 634, 128/664, 665; 422/82.05–82.08, 82.11; 436/86, 172; 356/39; 600/341, 342, 474, 476

[56] References Cited

U.S. PATENT DOCUMENTS

| | | | |
|---|---|---|---|
| 5,152,287 | 10/1992 | Kane | 128/634 |
| 5,341,805 | 8/1994 | Stavridi et al. | 128/634 |
| 5,350,375 | 9/1994 | Deckelbaum et al. | 128/634 |
| 5,354,825 | 10/1994 | Klainer et al. | 128/634 |
| 5,449,625 | 9/1995 | Kobayashi et al. | 436/518 |
| 5,453,359 | 9/1995 | Gargan et al. | 453/13 |
| 5,470,307 | 11/1995 | Lindall | 128/634 |
| 5,512,492 | 4/1996 | Herron et al. | 436/518 |
| 5,536,783 | 7/1996 | Olstein et al. | 128/634 |
| 5,626,134 | 5/1997 | Zuckerman | 128/634 |
| 5,640,470 | 6/1997 | Iyer et al. | 128/634 |

OTHER PUBLICATIONS

Kinsey et al., "Endoscopic System for Simultaneous Visual Exam . . . Fluorescence," Rev. Sci. Instrum., vol. 51, No. 10, Oct. 1980.

*Primary Examiner*—Linda C.M. Dvorak
*Assistant Examiner*—Bryan K. Yarnell
*Attorney, Agent, or Firm*—John P. Wooldridge

[57] ABSTRACT

A fiber optic sensor for D dimer (a fibrinolytic product) can be used in vivo (e.g., in catheter-based procedures) for the diagnosis and treatment of stroke-related conditions in humans. Stroke is the third leading cause of death in the United States. It has been estimated that strokes and stroke-related disorders cost Americans between $15–30 billion annually. Relatively recently, new medical procedures have been developed for the treatment of stroke. These endovascular procedures rely upon the use of microcatheters. These procedures could be facilitated with this sensor for D dimer integrated with a microcatheter for the diagnosis of clot type, and as an indicator of the effectiveness, or end-point of thrombolytic therapy.

30 Claims, 3 Drawing Sheets

FIBER OPTIC D DIMER BIOSENSOR

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to sensors for use in medical procedures, and more specifically, it relates to a fiber optic biosensor for the diagnosis and treatment of stroke-related conditions. More specifically, it relates to a biosensor which can be used in vivo in endovascular procedures, integrated with a catheter, for the diagnosis of thrombus (blood clot) type and to provide guidance in the use of thrombolytics for clot dissolution (e.g., dose and dose rate). It can be used in conjunction with other therapies, such as laser thrombolysis.

2. Description of Related Art

Stroke is the third leading cause of death in the United States, costing an estimated $15–30 billion per year. Most strokes are caused by vascular occlusion due to cerebral atherosclerosis or to thromboemboli of the extracranial or intracranial blood vessels. When vascular occlusions occur, such as in the carotid artery, blood flow to the brain is impeded, leading to stroke.

Interventional neuroradiologists and neurosurgeons have devised elegant procedures for treating stroke. Through use of microcatheters they are able to insert coils into aneurysms, perform balloon angioplasty on calcified deposits, and administer thrombolytic agents. Thrombolytic therapy is a minimally invasive procedure which involves directing a microcatheter to the site of an occlusion and releasing thrombolytic agents directly into a clot. If the clot is composed of cross-linked fibrin (i.e., soft vs. calcified) the clot will lyse producing fibrinolytic products. With regard to diagnosis, the most important of these fragments is D dimer, which is composed of crosslinked gamma chain remnants.

There is currently available an in vitro test for D dimer. This test, performed in hospital clinical laboratories is often ordered for patients presenting stroke symptoms. The test is based upon agglutination. A plasma sample from the patient's blood is mixed with a solution containing the antibodies supplied with the test kit. If the solution becomes cloudy (agglutinates), the presence of D dimer is indicated. The level of D dimer is determined (very roughly) by performing this test using successive dilutions of the patient's blood plasma. This test only determines the systemic presence of D dimer.

A sensor for D dimer would find widespread use as an important diagnostic tool in marking ischemic events. Used in vivo, it could obtain localized information in the vascular system. As a diagnostic tool, it would be valuable because it could distinguish, locally, whether an occlusion is caused by atherosclerotic plaque or thrombus. A D dimer sensor would be useful in providing guidance for dosage and infusion rates of thrombolytic agents. Most importantly, it should be usable in isolated therapy procedures (e.g., double balloon) to detect when a thrombus was completely lysed and whether restenosis was occurring following therapy.

Fiber optic sensors are well known in the literature. They have been used for environmental and medical applications. Enhancement of sensitivity and selectivity has been obtained using coatings applied to the fiber optic core. When used as biosensors, a biologically-active component is an integral part of the coating. If these biologically-active components are antibodies, then the biosensor is specifically an immunosensor. When immersed in the environment of interest, antigens diffuse into the coating and bind with the antibodies. The binding process forms the basis for detection. Specifically, if the antibodies are "tagged" with a fluorescent molecule, when the antigen binds there will be an effect on the spectroscopic properties of the "tagging" molecule. Fiber optic biosensors using this detection scheme are well known.

SUMMARY OF THE INVENTION

It is an object of the invention to provide a biosensor comprising an optical fiber with a coating on the end encapsulating antibodies to D dimer that have been tagged with a fluorescent molecule. The antibody to D dimer is mouse anti-human monoclonal antibody.

An antibody comprising mouse anti-human monoclonal antibody is "tagged" with a fluorescent molecule, for example fluorescein isothiocyanate (FITC). This antibody is encapsulated on the end of an optical fiber to produce a biosensor. A variety of molecules can be used to tag the antibody, leading to a wide range of accessible wavelengths to customize optical systems. The encapsulating material for the antibody, which is the major component of the end coating, is one of a variety of polymers, gels, or transparent sol-gel-derived materials. For example, the encapsulating coating may be a silica sol-gel, formed by sol-gel polymerization of tetraethoxysilane. Alternatively, it can be formed by the glutaraldehyde-induced cross-linking of bovine serum albumin. The "tagged" antibody is physically constrained within the coating as it is formed on the end of the fiber. There may be additional chemical interactions bonding the antibody in the coating.

DETAILED DESCRIPTION OF THE INVENTION

Figure 1:
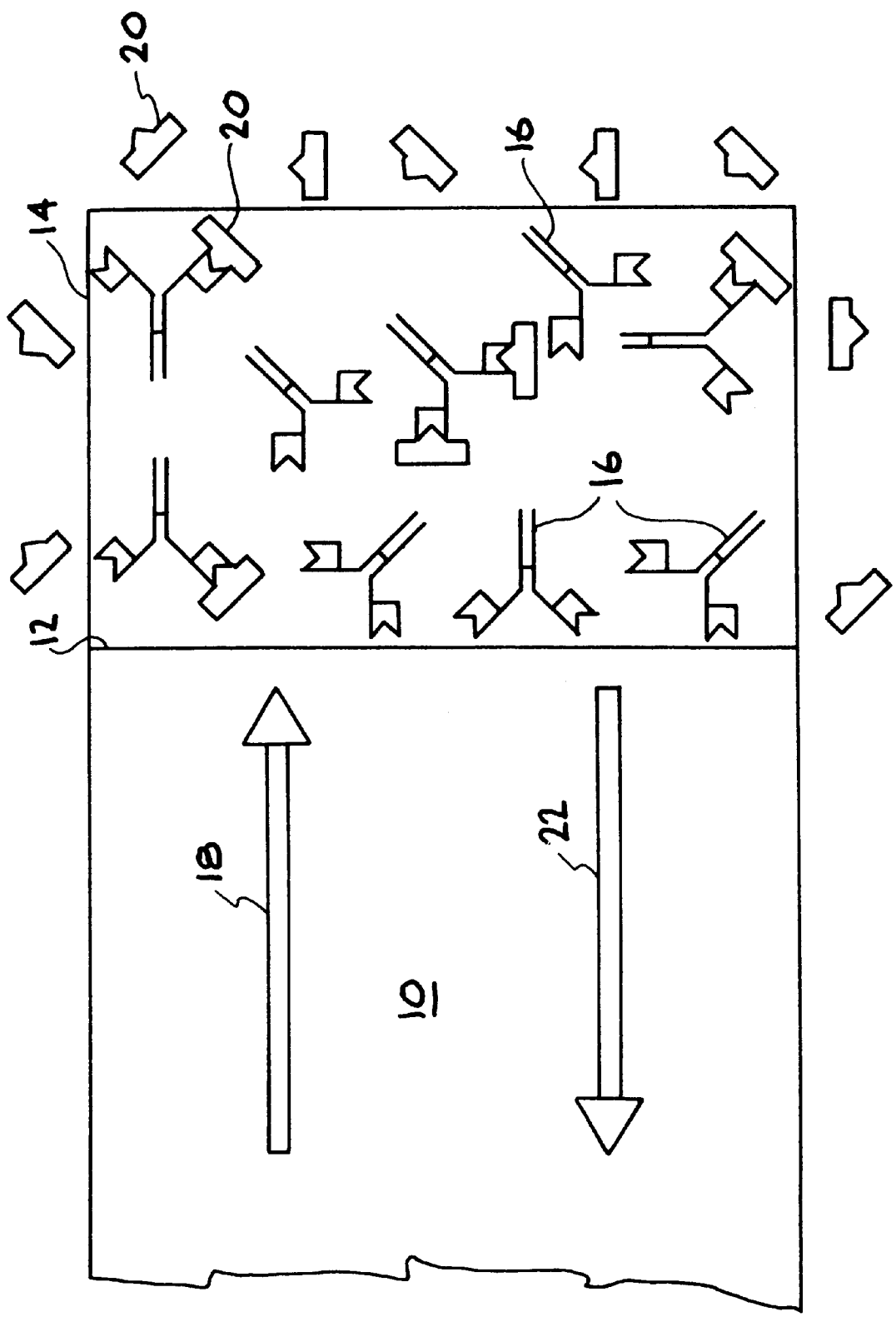
FIG. 1 shows the end of an optical fiber coated with a layer containing an antibody tagged with a fluorescent molecule.

FIG. 1 shows an embodiment of the invention having a fiber optic 10 with an end 12 having a coating 14 comprising antibodies 16 that have been tagged with a fluorescent molecule. Through fiber optic 10, light 18 from a polychromatic source illuminates and excites the tagging molecules of antibodies 16. As the antigen 20 (D dimer) diffuses into the coating 14 and binds with the antibodies 16, the fluorescence properties of the tagging molecule are altered. Generally this leads to intensity changes, or emission wavelength changes (which form the basis for sensing) resulting a fluorescence signal 22 that is partially collected by fiber optic 10 and delivered to a detection system.

Figure 2:
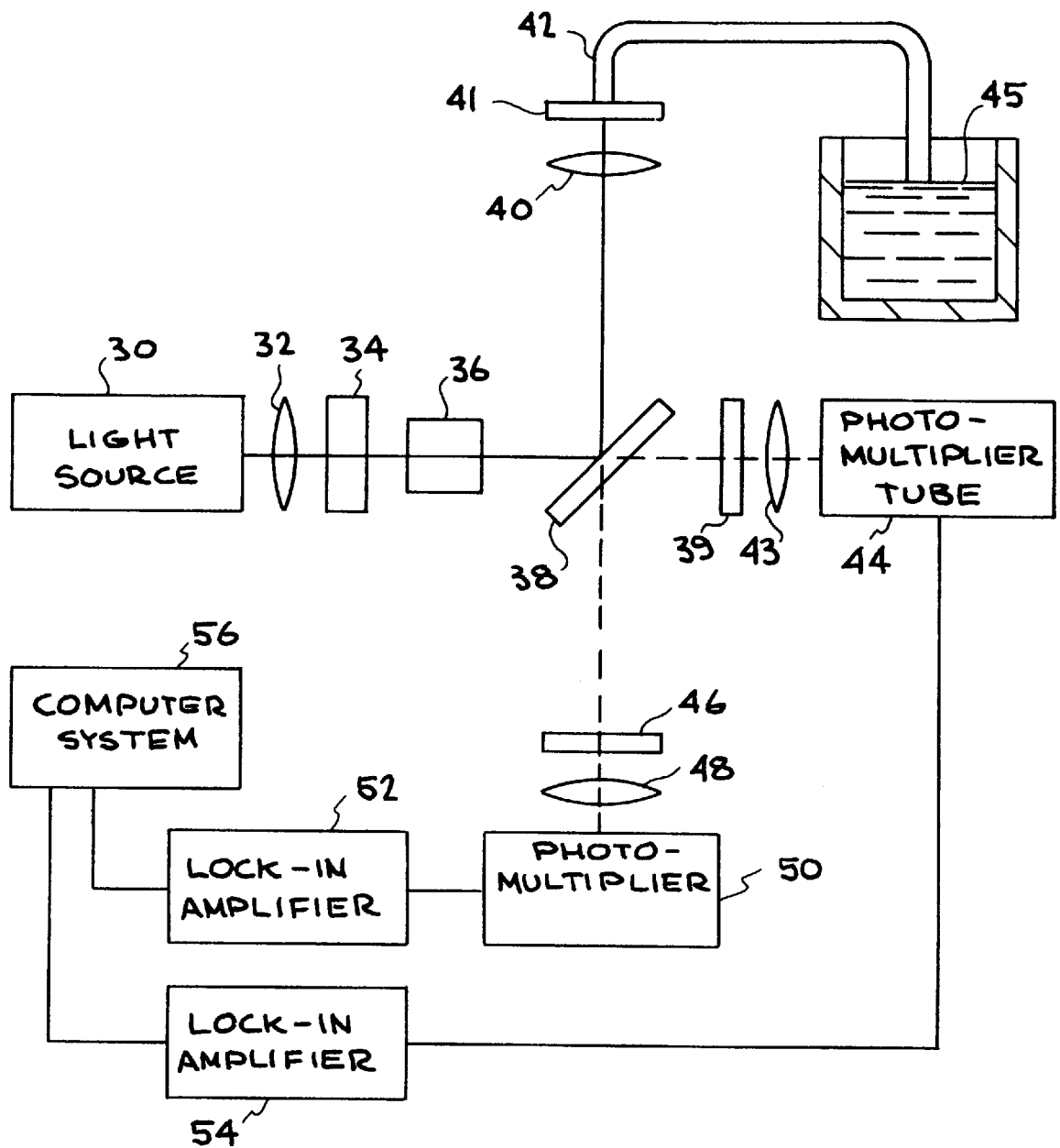
FIG. 2 shows an embodiment of the invention utilizing ratiometric measurements.

FIG. 2 shows an embodiment of the invention where ratiometric measurements are performed. Excitation is provided by a light source 30 such as a 12 W tungsten halogen lamp. The light is collimated by a biconvex lens 32 before passing through a bandpass filter 34 of wavelength 488±5 nm. The chopper wheel 36 may have variable speeds to modulate the excitation light. The light that is reflected by the dichroic mirror 38 (505 nm split) is coupled through a biconvex lens 40 (focal length of 4 cm), a filter 41 and an optical fiber 42 before entering into a blood sample 45. Some of the light will pass through the dichroic mirror 38 instead of being reflected. This light will pass through filter 39 and be coupled by biconvex lens 43 to a photomultiplier tube 44. The fluorescence signal returning through fiber optic 42, is collimated by lens 40 and passes through dichroic mirror 38 through filter 46 to be focused by biconvex lens 48 into photomultiplier 50. Each photomultiplier 44, 50, and the chopper 36 are interfaced to lock-in amplifiers 52, 54. The signal from each lock-in is sent to a computer 56 where ratio measurements are performed.

Another alternative system could utilize sample and hold circuits instead of the lock-in amplifiers. This substitution would make the system more compact. Also, instead of choppers and lock-ins, the detection system could include two avalanche photodiodes in the photon-counting mode. A timing chip on a lab tender board could be used to trigger an acousto-optic modulator and count the pulses from the photodiodes.

The fiber optic sensor can be used within (or integrated with) a catheter, which would be threaded through the vascular system up to the site of an occlusion. Fluorescence changes can be related to the local concentration of D dimer in the blood, ideally with the biosensor placed as close as possible next to, or within a thrombus. X-ray angiography is used to guide the placement of the tip of the catheter to the site of an occlusion.

The interventional neuroradiologist, endovascular surgeon, or neurosurgeon accesses the femoral artery and inserts the catheter through which the sensors and other tools (laser fibers, microgrippers, microballoons, etc.) for treating ischemic or hemorraghic stroke are inserted. Using real-time angiography, the catheter is threaded through the vascular system, through the aorta, to the site of the occlusion. The occlusion may reside in the carotid artery, or in smaller vessels in the brain. Once located, the physician has a variety of treatment options available for treating ischemic stroke. If the clot is fibrous, he can physically insert the catheter into the clot and deliver thrombolytic agents (such as rt-PA, urokinase, and streptokinase) through a tube placed within the catheter. If the clot is calcified, he can perform balloon angioplasty. Short laser pulses in conjunction with thrombolytics may be used to destroy the clot. The present invention is particularly useful for treatments using thrombolytics.

Clots in the vascular system can be classified in one of two ways. Either they are calcified (hard) or are fibrous (soft). This simple classification obscures the typical situation, as in most cases a clot will have some of both character. In particular, the older the clot, the more calcified it becomes. In any case, thrombolytics are effective in dissolving the fibrous part of the clot.

Local intra-arterial thrombolysis of acutely occluded blood vessels has potential for revascularization of ischemic cerebral territories. However, rapid diagnosis and initiation of the therapy are crucial in stroke patients to reduce brain tissue necrosis. Therefore, patients presenting with acute neurological deterioration undergo a full neurological evaluation and a battery of blood tests. A cerebral angiogram is performed to map out and identify the region in the brain suffering from the occlusion, any collateral circulation and the size and the extent of the occlusion. If the patient "passes" these tests, then thrombolytic therapy can be initiated. As mentioned above, thrombolytic therapy involves directing a microcatheter to the site of the occlusion and releasing the thrombolytic agents directly into the clot. The treatment is highly variable; i.e., different agents, infusion rates, and dosages are used at the attending physicians discretion. The optimal treatment plan for thrombolytic therapy has yet to be determined. One particular thrombolytic agent is rt-PA (recombinant tissue plasminogen activator). Currently, the most widely recommended dosage is 0.9 mg/Kg of body weight. Once injected, the thrombolytic agent acts upon the circulating plasma proenzyme, plasminogen, cleaving it to form the enzyme, plasmin. Plasmin binds directly to cross-linked fibrin (and also fibrinogen and non-crosslinked fibrin) and breaks it down. Only crosslinked fibrin (which forms the "web" of soft clots) due to its covalent bonding side-to-side and end-to-end of the fibrin chains, produce the degradation fragment called D dimer. Because the D dimer fragments possess antigenic properties, this has allowed the development of an in vitro diagnostic test kit referred to above. This kit contains a solution containing the antibody which specifically binds to the D dimer fragment.

The D dimer sensor having immobilized D dimer antibodies on the tip will bind with the D dimer fragments. Upon binding, the emission fluorescence will be quenched at a level linearly related to the concentration of D dimer fragments. It is the object then that this sensor could provide feedback on the dosage and infusion rate of the thrombolytic agent. If there are no D dimer fragments, i.e., the thrombolytic agent did not lyse the clot, indicating that it was largely calcified, then this treatment can be ceased and a new treatment plan could be quickly undertaken.

To help eliminate the guesswork involved in thrombolytic therapy, a D dimer sensor could be directed to the clot and used for clot type diagnosis and to provide guidance in therapeutic intervention. In particular, the sensor would identify whether the clot was "soft", which would indicate the use of thrombolytics. Alternative therapies would be suggested if the clot was primarily calcified. If thrombolytics are used, the sensor can be placed near (or into) the clot and be used to detect the end point of therapy.

A particularly effective form of therapy would involve a "double balloon" procedure. In this procedure, the clot would be isolated by inflating a catheter-delivered microballoon on either side of the clot. Thrombolytics would then be delivered into this local "microenvironment". The sensor would be used to direct delivery rate and total dose of the thrombolytic. That is, when the sensor detects no further release of D dimer, indicating complete lysing of the clot, the treatment should be halted. Using the sensor in this way would avoid delivery of too much thrombolytic agent, thereby minimizing the negative effects of the drug (hemorrhage).

The sensor could also be used in conjunction with laser thrombolytic treatments for clot removal. It could be used to provide guidance in use of the laser. For example, pulse length, energy, etc.

There are several issues to be considered with regard to choice of fibers and materials to use in construction of a D dimer sensor. For instance, considerations involving the optical fiber include: composition, size, numerical aperture, tip configuration of the fiber, and the coating method. For an encapsulating/coating material one could use a polymer such as polyurethane or copolymer of polyurethane, hydrogels, sol-gel coatings, etc. There are a number of coating parameters which affect sensor response, such as thickness of the coatings, dopant levels, pore sizes of the coatings, etc.

Typical fiber materials which can be used in construction of a D dimer sensor include fused silica and polymethlymethacrylate (PMMA). Typically, these fibers are 125 mm in diameter, although fibers both larger and smaller than this can be used (50–250 $\mu$m). The fibers are multimode with conventional numerical apertures of 0.499 for the silica fibers and 0.47 for the PMMA fibers.

A variety of tip configurations are utilized in order to achieve maximum coupling of fluorescence back down the fiber. One method involves stripping the fiber of its cladding and tapering the end of the fiber in an appropriate etching solution. This method allows for evanescent wave sensing. Another geometry uses blunt-end fibers with their claddings intact, which are prepared by polishing perpendicular to the axis of the fiber. Another configuration involves leaving the cladding intact and etching out the core using an appropriate etchant solution. Side-firing fibers are also prepared by polishing the tips at a 45 degree angle. One way of using side firing fibers (50 $\mu$m diameter) is to place two side-by-side. One fiber carries the excitation light and the other carries the emission fluorescence.

A variety of fluorescent molecules can be used to tag the antibodies. One particularly common tag is fluorescein isothiocyanate (FITC). The tagged molecules used to obtain the data reported below were purchased from Biogenesis, Inc. (Sandown, N.H.). The method they use to synthesize the FITC-labeled antibodies is proprietary; however, they state that it is non-covalent and adapted from the literature. The use of tagging procedures is considered fairly routine. Various procedures are used, and are discussed elsewhere (see, for example, A. Feteanu, "Labeled Antibodies in Biology and Medicine," Abacus Press, McGraw–Hill, New York, 1978, pp. 61–66).

The tagged antibodies are mixed with the encapsulant coating material which is dip coated onto the tip of a fiber. Two representative methods for preparing the fibers are described below.

The silica sol-gel method involves preparing a sol solution, mixing in the D dimer antibodies, dip coating the fiber, and then letting it dry into a solid glass coating. To prepare the sol-gel solution, TMOS (tetramethoxysilane), deionized, distilled water, and an acid catalyst are sonicated in an ice bath for thirty minutes. To this sol solution, phosphate buffer saline is added in order to increase the pH of the solution, creating a favorable environment for the D dimer antibodies. As a last step before dip coating the fibers, the D dimer antibodies are added. The sol-gel coating on the fiber is approximately 1 $\mu$m. Any thickness above this causes the coating to crack and flake off upon drying. The sol-gel will shrink to approximately ⅛ of its original volume. This shrinkage will effectively increase the concentration of the D dimer antibodies to approximately the $10^{-5}$ M region.

Polymer coatings can also generally be applied by dip coating. For example, ChronoFlex™ AR (PolyMedica Biomaterials, Inc., Golden, Colo.) is a biocompatible polyurethane which comes in viscous solution form. These materials can be mixed with the D dimer antibodies and dip coated onto a fiber tip. The coating can then be dried in air, or preferably, at somewhat elevated temperature (e.g., 70–80° C.). Since the coating solution is more viscous than the sol solution, the coatings are thicker. In order to minimize diffusion times (of antigen into the coating), efforts should be taken to keep total coating thickness less than 10 $\mu$m, and preferably 1–2 $\mu$m and below. That is, the loading and thickness of the coating should be optimized to provide sufficient fluorescence signal while also providing an acceptable response time.

Hydrogels are soft, biocompatible polymeric materials which can absorb more than 40% of their weight in water. P-HEMA (poly(2-hydroxyethyl methacrylate) is one hydrogel which can be mixed with the antibodies and used to coat fibers, again by dip coating.

Cross-linked bovine serum albumin (initiated with glutaraldehyde) can also be used as an encapsulant/coating for the fiber. A weighed sample of bovine albumin (usually 10 mg) is mixed with PBS (usually 100 ml). To this is added the D dimer antibodies. Glutaraldehyde (usually 10 ml) is then added to this solution. The fiber is then quickly dip coated.

A combination of the coating methods can also be utilized. For instance, sol solutions can be applied after first dip coating the fiber in D dimer-doped polyurethane coatings. Within the coating itself, the concentration of the fluorescent tagged D dimer antibody can be variable. Typically, it is at micromolar concentrations.

The mechanism of sensing action is straightforward. When placed in a fluid medium, such as water, plasma, or blood, the D dimer will diffuse into the coating on the end of the fiber. The antigen binds with the tagged antibody, causing a change in the fluorescence properties of tagging molecules. This change can be a wavelength shift, or a change in emission intensity. In the case of the FITC-labeled D dimer antibodies, the result is a substantial decrease in fluorescence intensity.

Figures 3, 4:
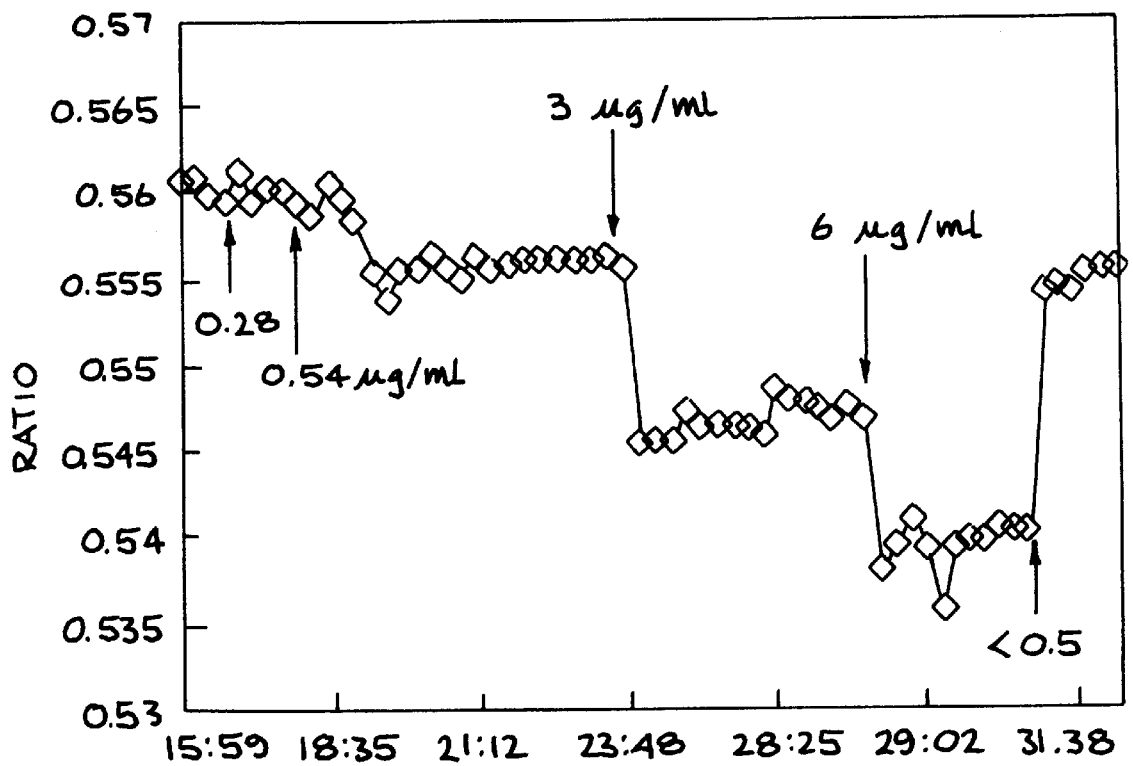
FIG. 3 shows a chart of a sample test using a D-Di test kit.
FIG. 4 shows data for the response of the sensor as a function of time for addition of increasing amounts of D dimer to human blood.

The sensor response is calibrated against a D-Di test kit (donated by American Bioproducts Company, Parsippany, N.J.). The minimum detectable level of D dimer antigens for the in vitro diagnostic kit is approximately 0.25 $\mu$g/ml. Healthy individuals have levels of D dimer below this level. FIG. 3 shows a chart of a sample test using a D-Di test kit. The test sample is undiluted blood which is diluted with phosphate buffer solution (PBS). (+) indicates a positive identification of D dimer fragments while (−) gives a negative indication of the fragments.

A typical experimental set-up for the fiber optic biosensor uses the configuration shown in FIG. 2. A 125 mm silica fiber is dipped coated into a sol-gel solution containing 1.31 $\mu$M D dimer antibodies tagged with FITC. (The final concentration of D dimer antibodies after shrinkage is approximately 10 $\mu$M.) The fiber tip is placed in a 2 mL vial of A (+) human blood. The FITC labels are excited by 485 nm incident wavelength light and will fluoresce at 520 nm. Since the presence of D dimer antigens will quench the FITC fluorescence, (+) control D dimer antigens were added to the 2 ml of blood in 100 $\mu$l increments. A decrease in fluorescence was first recorded when 200 $\mu$l of D dimer antigens were in 2 ml of blood. This represents a concentration of D dimer of 0.26 $\mu$g/ml. Decreases in fluorescence were recorded up to an essentially 100% D dimer antigen solution. The fiber was placed in water and a slight rebound of fluorescence was recorded. The data may be interpreted by a linear decrease in fluorescence with increasing amounts of the D dimer antigen.

Additional data is shown FIG. 4. These data display the response-time plot for addition of increasing amounts of D dimer to blood. A decrease of flourescence is noted with increasing concentration. A large rebound in signal is noted when the sample is diluted with fresh blood, making the concentration of D dimer less than 0.5 $\mu$g/ml.

From a stroke treatment perspective, as thrombolytic agents are injected into the clot and the degradation of the clot is initiated, the rate of D dimer antigen production will reach a peak and then decline. This process could be monitored using the D dimer sensors, integrated with the catheter along with the tube for thrombolytic delivery and fibers for laser thrombolysis.

Changes and modifications in the specifically described embodiments can be carried out without departing from the scope of the invention, which is intended to be limited by the scope of the appended claims.

We claim:

1. A D dimer biosensor for the diagnosis and treatment of stroke and stroke-related conditions, comprising:
   a fiber optic having a proximal end and a distal end;
   a coating affixed to said distal end of said fiber optic, wherein said coating comprises P-HEMA (poly(2-hydroxyethyl methacrylate));
   mouse anti-human monoclonal antibody that has been tagged with a fluorescent molecule, wherein said coating encapsulates said mouse anti-human monoclonal antibody, wherein said D dimer biosensor is used for the diagnosis and treatment of stroke and stroke-related conditions.

2. The D dimer sensor of claim 1, wherein said fluorescent molecule comprises fluorescein isothiocyanate (FITC).

3. The D dimer sensor of claim 2, wherein said FITC is excited by 485 nm incident wavelength and fluoresces at 520 nm wavelength.

4. The D dimer sensor of claim 1, wherein said coating is selected from a group consisting of a polymers, a gel and a transparent sol-gel-derived material.

5. The D dimer sensor of claim 4, wherein said coating is selected from a group consisting of (i) a material produced from sol-gel polymerization of tetraethoxysilane, (ii) a material produced from sol-gel polymerization of tetramethoxysilane, (iii) glutaraldehyde-induced cross-linking of bovine serum albumin, (iv) a hydrogel and (v) a polyurethane.

6. The D dimer sensor of claim 4, wherein said polymer is selected from a group consisting of polyurethane and copolymer of polyurethane.

7. The D dimer sensor of claim 1, further comprising:
   a light source;
   means for focusing a beam from said light source into said fiber optic; and
   means for detecting fluorescence emitted from said fluorescent molecule,
   wherein D dimer antigen diffuses into said coating when said distal end of said fiber optic is inserted into a sample comprising said antigen, wherein said antigen binds with said antibodies, wherein the fluorescence properties of said tagging molecule are altered which causes intensity changes, or emission wavelength changes (which form the basis for sensing) resulting in a fluorescence signal that is partially collected by said fiber optic and delivered to said means for detecting said fluorescence emitted from said fluorescent molecule.

8. The D dimer sensor of claim 7, wherein said light source is selected from a group consisting of a monchromatic light source and a polychromatic light source.

9. The D dimer sensor of claim 7, wherein said light source is selected from a group consisting of a tungsten halogen lamp, a light emitting diode and a laser diode.

10. The D dimer sensor of claim 7, wherein said means for detecting fluorescence emitted from said fluorescent molecule comprise:
    a chopper producing a reference frequency;
    a first lock-in amplifier having a first reference frequency input channel, a reference input channel and a reference output channel for producing a reference output;
    a second lock-in amplifier, having a second reference frequency input channel, a signal input channel and a signal output channel for producing a signal output;
    a reference detector electrically connected to said reference input channel; and
    a signal detector electrically connected to said signal input channel, wherein said chopper reference frequency is electrically connected to said first reference frequency input channel and said second reference frequency input channel, wherein said signal output is divided by said reference output to provide discrimination against background to improve the signal-to-noise ratio.

11. The D dimer sensor of claim 7, further comprising a catheter, wherein said fiber optic is located within said catheter.

12. The D dimer sensor of claim 11, wherein said catheter comprises means for delivery of thrombolytic agents to a blood clot.

13. The D dimer sensor of claim 12, wherein said means for delivery of thrombolytic agents to a blood clot comprise a tube located within said catheter.

14. The D dimer sensor of claim 12, wherein said thrombolytic agents are selected from a group consisting of recombinant tissue plasmingen activator (rt-PA), urokinase and streptokinase.

15. The D dimer sensor of claim 14, wherein said rt-PA is administered at a dosage of 0.9 mg/Kg of body weight.

16. The D dimer sensor of claim 7, wherein said means for detecting fluorescene emitted from said fluorescent molecule are selected from a group consisting of lock-in amplifiers and sample and hold circuits.

17. The D dimer sensor of claim 7, wherein said means for detecting fluorescence emitted from said fluorescent molecule includes two avalanche photodiodies in the photon-counting mode.

18. The D dimer sensor of claim 7, wherein said means for detecting fluorescence emitted from said fluorescent molecule include a timing chip on a lab tender board to trigger an acousto-optic modulator and count the pulses from two avalanche photodiodes in the photon counting mode.

19. The D dimer sensor of claim 1, wherein said fiber optic comprises a substrate from a group consisting of fused silica and polymethlymethacrylate (PMMA).

20. The D dimer sensor of claim 1, wherein said fiber optic comprises a configuration selected from a group consisting of a fiber stripped of its cladding and tapered at an end of said fiber optic, a blunt-end fiber, a fiber having its core etched away and a side-firing fiber having its tip polished at a 45 degree angle.

21. The D dimer sensor of claim 20, wherein said fiber optic comprises a diameter with a range from 50 $\mu$m to 300 $\mu$m.

22. A method of detecting D dimer, comprising:
    inserting a D dimer sensor into a blood sample, wherein said D dimer sensor comprises a fiber optic having a coating affixed to a first end thereof, wherein said coating comprises mouse anti-human monoclonal antibodies that have been tagged with fluorescent molecules;
    directing a beam of light into a second end of said fiber optic, wherein said beam of light excites said fluorescent molecules to produce fluorescence which is collected by said fiber optic and exits said second end of said fiber optic, wherein said fluorescence is amplitude modulated; and detecting said fluorescence by a detector that is electrically connected to the signal input channel of a lock-in amplifier, wherein a reference frequency is electrically connected to the reference channel of said lock-in amplifier, wherein said lock-in amplifier provides an analog signal output that is proportional to the intensity of said fluorescence that is detected by said photodiode, wherein the step of inserting a D dimer sensor into a blood sample includes inserting a D dimer sensor within a catheter into the arteriovenous system by threading said catheter through the vascular system up to the site of an occlusion, wherein fluorescence changes can be related to the local concentration of D dimer in the blood, ideally with the biosensor placed as close as possible to, or within a thrombus.

23. The method of claim 22, further comprising the step of using real-time x-ray angiography to guide the placement of said first end of said fiber optic to the site of an occlusion.

24. The method of claim 23, further comprising the step of accessing the femeral artery of a patient and inserting said catheter.

25. The method of claim 24, further comprising the step of delivering thrombolytic agents through a tube placed within said catheter.

26. The method of claim 25, wherein the step of delivering thrombolytic agents includes delivering thrombolytic agents selected from a group consisting of rt-PA, urokinase and streptokinase.

27. The method of claim 25, further comprising the step of directing short laser pulses through said fiber optic to a clot.

28. The method of claim 27, further comprising the step of using thrombolytics in conjunction with said short laser pulses to destroy said clot.

29. The method of claim 28, further comprising the step of isolating said clot by inflating a catheter-delivered microballoon on either side of said clot, wherein the rate at which thrombolytics are delivered into this local "microenvironment" can be controlled to prevent hemorrhage using the D dimer sensor.

30. A D dimer biosensor, comprising:

a fiber optic having a proximal end and a distal end;

a coating affixed to said distal end of said fiber optic, wherein said coating comprises P-HEMA (poly(2-hydroxyethyl methacrylate);

mouse anti-human monoclonal antibody that has been tagged with a fluorescent molecule, wherein said coating encapsulates said mouse anti-human monoclonal antibody;

a light source for producing a beam of light;

a chopper for chopping said beam of light, said chopper producing a reference frequency;

a dichroic mirror for reflecting a first portion of said beam, wherein said dichroic mirror transmits a second portion of said beam;

a lens for focusing said first portion into said proximal end;

a first lock-in amplifier having a first reference frequency input channel, a reference input channel and a reference output channel for producing a reference output;

a second lock-in amplifier, having a second reference frequency input channel, a signal input channel and a signal output channel for producing a signal output;

a reference detector for detecting said second portion of said beam, wherein said reference detector is electrically connected to said reference input channel;

wherein antigen (D dimer) diffuses into said coating when said distal end of said fiber optic is inserted into a sample comprising said antigen, wherein said antigen binds with said antibodies, wherein the fluorescence properties of said tagging molecule are altered which causes intensity changes, or emission wavelength changes (which form the basis for sensing) resulting in a fluorescence signal that is partially collected by in said distal end of said fiber optic and exits said proximal end of said fiber optic to produce a signal beam; and a signal detector for detecting said signal beam, wherein said signal detector is electrically connected to said signal input channel, wherein said reference frequency from said chopper is electrically connected to said first reference frequency input channel and said second reference frequency input channel, wherein said signal output is divided by said reference output to provide discrimination against background to improve the signal-to-noise ratio.

* * * * *